United States Patent [19]

Bartholdson

[11] Patent Number: 4,507,810
[45] Date of Patent: Apr. 2, 1985

[54] IMPLANTABLE BREAST PROSTHESES

[75] Inventor: Lennart O. Bartholdson, Umea, Sweden

[73] Assignee: Polar-Plastik HB, Umea, Sweden

[21] Appl. No.: 343,930

[22] Filed: Jan. 29, 1982

Related U.S. Application Data

[63] Continuation-in-part of Ser. No. 122,767, Feb. 19, 1980, abandoned.

[30] Foreign Application Priority Data

Feb. 19, 1979 [SE] Sweden .................... 7901424

[51] Int. Cl.³ .................................. A61F 1/00
[52] U.S. Cl. .......................... 3/36; 128/462; 128/481
[58] Field of Search ............ 3/36; 128/425, 462, 128/478, 479, 481, 492

[56] References Cited

U.S. PATENT DOCUMENTS

| | | | |
|---|---|---|---|
| 2,542,619 | 2/1951 | Bernhardt | 3/36 |
| 3,366,975 | 2/1968 | Pangman | 3/36 |
| 3,986,213 | 10/1976 | Lynch | 3/36 |

Primary Examiner—Richard J. Apley
Assistant Examiner—David Isabella
Attorney, Agent, or Firm—Fleit, Jacobson, Cohn & Price

[57] ABSTRACT

An implantable breast prosthesis having a shell of biocompatible material filled with a plurality of individual, irregularly shaped cells. The shell is at least partially filled with a liquid. The cells have passageways formed therein, that preferably have different sizes, to provide fluid communication between the cells so that the liquid flows in a manner to simulate natural breast movements. Cells are interconnected with the shell and with each other so as to avoid excessive movement.

4 Claims, 1 Drawing Figure

U.S. Patent   Apr. 2, 1985   4,507,810
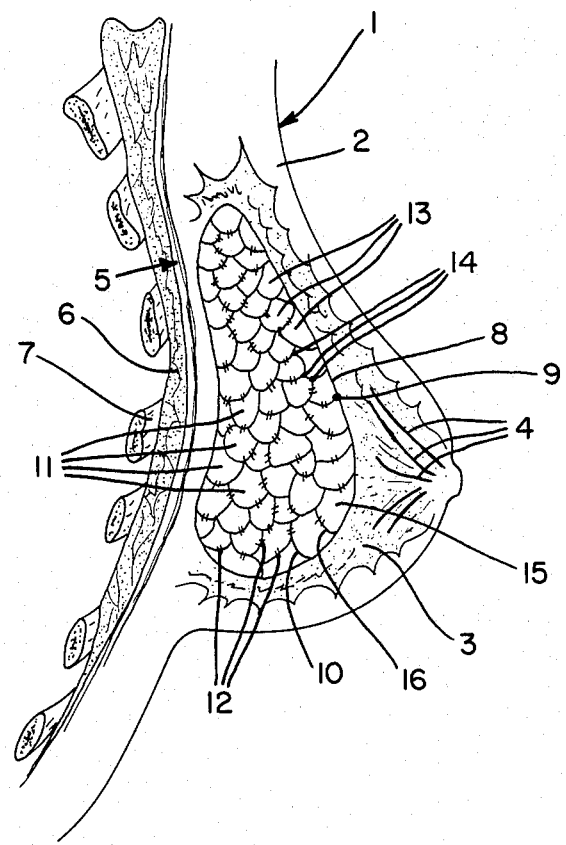

IMPLANTABLE BREAST PROSTHESES

CROSS-REFERENCE TO RELATED APPLICATION

This application is a continuation-in-part application of U.S. patent application Ser. No. 122,767, filed Feb. 19, 1980 now abandoned.

BACKGROUND OF THE INVENTION

1. Field of the Invention

This invention concerns a breast prosthesis which, on being inserted, is intended to enlarge the breast.

2. Description of the Prior Art

Body-promoting breast prostheses which are intended to enlarge the female breast by being inserted under the skin in order to resemble the normal female breast in shape and size are to be found already today. These are on the whole of three different kinds.

The first kind is the so-called Cronin-prosthesis, consisting of a thin shell of Silastic and containing a kind of jelly-type Silastic. This prosthesis has been marketed since 1962. A disadvantage of this prosthesis is that the jelly leaks out, leaving a scar capsule round the prosthesis.

The second kind of prosthesis consists of a shell with Silastic in which the prosthesis space has been filled up with a salt solution. The difficulty encountered here is that the breast has become somewhat splashy and, at least at the outset, there is a risk that air can enter when the prosthesis is being filled with a salt solution, and, due to this cause the prostheses tends to squelch when the female person is walking.

The third and final type of prosthesis is a combination of the two prostheses described above and in which the inner core consists of Silastic-jelly, and, outside this, a salt solution fills up the remaining cavity, and, outside this, a shell with Silastic. Not even this type is satisfactory.

Previously known implantable prosthesis are described in U.S. Pat. Nos. 3,366,975, 3,559,214, 3,683,424, and 3,986,213. It should be noted that these patents describe different types of material available for use in the manufacture of prosthesis.

SUMMARY OF THE INVENTION

An aim of the present invention is to bring about a better prosthesis that will eliminate the disadvantages connected with the existing prostheses.

It is important to make a prosthesis resembling as much as possible the body's own tissue. A female breast contains partly breast gland tissue, and partly fat. This means that a normal breast does not feel exactly homogenous throughout, but is soft and changes shape in keeping with the woman's changes of position—upright and recumbent—and so forth.

The prosthesis, according to the present invention, will alter shape when the woman changes position, thus giving a feeling of natural movement. It will also be possible to have the prosthesis made in factories, thus avoiding the problems that arise in connection with the filling of prostheses at insertion. Moreover, it will be less expensive to make than the existing prostheses.

The prosthesis provided by the present invention has an outer shell shaped to conform with the desired amount of breast enhancement desired. A rear surface of the prosthesis is complementary to the curvature of the portion of the chest contacted by the prosthesis. The material forming the shell, which can be any of the well known biocompatible materials, is semi-rigid so that the prosthesis tends to maintain its normal shape, yet is sufficiently flexible to allow the shell to change shape when the wearer changes position.

The invention, and its objects and advantages, will become more apparent in the detailed description of the preferred embodiment hereinafter presented.

BRIEF DESCRIPTION OF THE DRAWING

One embodiment of the present invention will now be described in more detail with reference to the attached drawing, which is a schematic sectional view illustrating one embodiment of the invention in an implanted position.

DESCRIPTION OF THE PREFERRED EMBODIMENT

The present description will be directed in particular to elements forming part of, or cooperating more directly with, the present invention. Elements not specifically shown or described herein are understood to be selectable from those known in the art.

Referring now to the drawing FIGURE, an embodiment of the prosthesis provided by the present invention is illustrated in an implanted position within a breast. The breast has an outer skin layer 1 covering a layer of subcutaneous fat 2. Mammary gland tissue 3 surrounds the inserted breast prostheses in the front and on the sides. The mammary gland descents are identified with the reference numeral 4. The rear of the prosthesis is adjacent the big breast muscle 5, which is in front of the chest 6 and ribs 7.

Considering now the prosthesis provided by the present invention, it has an outer wall 8 formed of a biocompatible material. A plurality of individual, irregularly shaped individual cells 10 and 11 are encompassed within the shell 8. It should be noted that the sizes of the cells vary so as to provide more natural movement. At least some of the cells adjacent the shell 8 are firmly affixed thereto, as identified by the reference numeral 9. Each of the cells has at least one passageway 12 formed therein to provide fluid communication between the individual cells. The locations and sizes of the passageways vary to provide easy flow of fluid between the cells so that the movement of the prosthesis is similar to that of a natural breast. To avoid excessive movement of the individual cells, adjacent cells are connected to each other, as represented by the connection points 14. The density of packing of the cells within the shell 8 is such that adjacent cells have walls in contact with each other, as identified by the reference numeral 16.

This prosthesis is filled with a solution of low viscosity or a fluid that must be bio-compatible or body-tissue-friendly. The amount of liquid added to the shell 8 and the viscosity of the liquid are determined by several factors. First, the weight of the prosthesis should be approximately the same as the weight of a normal breast. Second, the liquid must be able to slowly flow between adjacent cells to simulate natural movement. If the liquid flows too freely, undesirable splashing sounds occur. If the liquid flows too slowly, the breast is too rigid and does not move in a natural manner. On account of the prosthesis in question consisting of a cell system, it takes on a more natural performance and feeling, and, in addition, there is formed beneath the skin a more natural shape resembling the body's own tissue in the female breast. This prosthesis will change its shape when the women changes her position, and she will thus also feel more natural.

From the preceding, it can be seen that the present invention provides a breast prosthesis that is intended to be inserted in the female breast. The prosthesis has a thin shell 8 that contains a large number of individual cells. The shell 8 is partially filled with a very thin liquid, a body-tissue compatible solution, or a liquid with low viscosity. Passageways are formed in the cells so that the cells are in fluid communication with each other.

In the illustrated embodiment, adjacent walls of the cells are affixed to each other and the passageways in the cell walls are in alignment with each other. Any well known technique is usable to affix the cell walls to each other and to the shell, for instance, ultrasonic welding or glueing. It is also within the scope of the invention to assemble the cellular structure from cells having plastic walls that adhere to each other, with the assembled cellular structure being subjected to a subsequent curing operation. The passageways interconnecting the cells are formed either before or after the walls of the cells are affixed to each other. Further, the cells can be connected to each other and to the shell only at junction points. In such case, there is no need to align the passageways in the walls of adjacent cells.

The present invention has been described in only one representative embodiment, but it should be apparent that the invention can be varied in a variety of ways within the framework of the following claims.

What is claimed is:

1. An implantable breast prosthesis comprising:
   a flexible shell formed of bio-compatible material;
   a plurality of individual, irregularly shaped cells of different sizes defined by cell walls and encompassed within and completely filling said shell, with adjacent cells having walls in contact and attached with each other, each cell containing a liquid material and having at least one passageway formed in the cell wall and in direct communication with a passageway formed in the cell wall of an adjacent cell to provide fluid communication between adjacent cells; and
   a liquid partially filling said shell and cells, said passageways formed in the cell walls permitting movement of the liquid from one cell to an adjacent cell so that the liquid flows between the cells to simulate natural breast movements.

2. An implantable breast prosthesis according to claim 1, wherein at least some of the cells adjacent to said shell are firmly affixed thereto.

3. An implantable breast prosthesis according to claim 1 or 2, wherein adjacent cells are connected to each other.

4. An implantable breast prosthesis according to claim 1 or 2, wherein the passageways formed in the cell walls are of different sizes to provide different rates of liquid flow between the adjacent cells.

* * * * *